(12) United States Patent
Kojima et al.

(10) Patent No.: US 11,590,534 B2
(45) Date of Patent: Feb. 28, 2023

(54) ULTRASONIC SENSOR, ULTRASONIC DEVICE, AND METHOD OF MANUFACTURING ULTRASONIC SENSOR

(71) Applicant: Seiko Epson Corporation, Tokyo (JP)

(72) Inventors: Chikara Kojima, Matsumoto (JP); Hironori Suzuki, Chino (JP); Kanechika Kiyose, Matsumoto (JP)

(73) Assignee: SEIKO EPSON CORPORATION

( * ) Notice: Subject to any disclaimer, the term of this patent is extended or adjusted under 35 U.S.C. 154(b) by 1045 days.

(21) Appl. No.: 16/280,098

(22) Filed: Feb. 20, 2019

(65) Prior Publication Data

US 2019/0255568 A1    Aug. 22, 2019

(30) Foreign Application Priority Data

Feb. 21, 2018   (JP) .............................. JP2018-028546

(51) Int. Cl.
| | |
|---|---|
| *B06B 1/06* | (2006.01) |
| *B06B 1/02* | (2006.01) |
| *H01L 41/04* | (2006.01) |
| *H01L 41/047* | (2006.01) |
| *H01L 41/053* | (2006.01) |
| *H01L 41/187* | (2006.01) |
| *H01L 41/29* | (2013.01) |
| *H01L 41/318* | (2013.01) |

(Continued)

(52) U.S. Cl.
CPC .......... *B06B 1/0662* (2013.01); *B06B 1/0207* (2013.01); *B06B 1/0622* (2013.01); *H01L 41/042* (2013.01); *H01L 41/0477* (2013.01); *H01L 41/0533* (2013.01); *H01L 41/0825* (2013.01); *H01L 41/1876* (2013.01); *H01L 41/29* (2013.01); *H01L 41/318* (2013.01); *H01L 41/332* (2013.01); *H01L 41/335* (2013.01); *A61B 8/14* (2013.01)

(58) Field of Classification Search
CPC . B06B 1/0662; B06B 1/0207; H01L 41/0825; H01L 41/1876
See application file for complete search history.

(56) References Cited

U.S. PATENT DOCUMENTS

| | | | |
|---|---|---|---|
| 2006/0158066 A1 | 7/2006 | Soken | |
| 2007/0046152 A1* | 3/2007 | Ifuku | ................. H01L 41/1876 310/358 |

(Continued)

FOREIGN PATENT DOCUMENTS

| | | |
|---|---|---|
| JP | 2001-251159 A | 9/2001 |
| JP | 2004-304193 A | 10/2004 |

(Continued)

*Primary Examiner* — Bryan P Gordon
(74) *Attorney, Agent, or Firm* — Harness, Dickey & Pierce, P.L.C.

(57) ABSTRACT

An ultrasonic sensor includes a vibration plate that includes a vibration portion and is formed of a resin; a wall portion that is provided on the vibration plate, surrounds the vibration portion and is formed of a resin; and a piezoelectric element that is provided in the vibration portion of the vibration plate. Accordingly, the wall portion surrounding the vibration portion can suppress a frequency variation of an ultrasonic wave output from the ultrasonic sensor and can deform the ultrasonic sensor into a shape corresponding to a surface of an object having various shapes.

8 Claims, 11 Drawing Sheets

(51) Int. Cl.
*H01L 41/332* (2013.01)
*H01L 41/335* (2013.01)
*H01L 41/08* (2006.01)
*A61B 8/14* (2006.01)

(56) References Cited

U.S. PATENT DOCUMENTS

2014/0157902 A1\* 6/2014 Sugiura .................. G01S 15/50
    73/627
2015/0258573 A1\* 9/2015 Kojima ................ G10K 11/002
    310/327
2016/0282454 A1\* 9/2016 Ohashi .................... H01L 41/25

FOREIGN PATENT DOCUMENTS

| JP | 2004-312395 A | 11/2004 |
| JP | 2006-203563 A | 8/2006 |
| JP | 2012-015758 A | 1/2012 |
| JP | 2015-188208 A | 10/2015 |
| JP | 2017-128691 A | 7/2017 |

\* cited by examiner

ULTRASONIC SENSOR, ULTRASONIC DEVICE, AND METHOD OF MANUFACTURING ULTRASONIC SENSOR

BACKGROUND

1. Technical Field

The present invention relates to an ultrasonic sensor, an ultrasonic device, and a method of manufacturing the ultrasonic sensor.

2. Related Art

In the related art, there is known an ultrasonic sensor in which a vibration plate is provided so as to cover an opening provided in a substrate and a piezoelectric element is provided on the vibration plate (for example, JP-A-2015-188208).

As the ultrasonic sensor drives the piezoelectric element, the vibration plate vibrates, and thereby, an ultrasonic wave can be transmitted. In addition, as the piezoelectric element detects the vibration occurring when the ultrasonic wave is input to the vibration plate, reception of the ultrasonic wave can be detected.

In the ultrasonic sensor disclosed in JP-A-2015-188208, a frequency of the ultrasonic wave to be transmitted is defined by a dimension of a vibration portion, which is vibrated by the piezoelectric element in the vibration plate, in a shorter axis direction. Thus, in order to define the frequency of the ultrasonic wave to be transmitted, a configuration is provided in which the vibration portion is required to be set, an opening having a size corresponding to the vibration portion is provided on the substrate configured with Si or the like, and the opening is covered by the vibration plate.

However, an ultrasonic sensor for which a substrate such as Si is used has a poor flexibility, for example it is difficult to dispose the ultrasonic sensor on a surface of a curved object, and if the ultrasonic sensor is forcibly bent, the substrate formed of Si may be broken. Furthermore, in the ultrasonic sensor described in JP-A-2015-188208, the vibration plate covering the opening of the substrate is configured by a stacked body of $SiO_2$ and $ZrO_2$. Thus, if the ultrasonic sensor is bent, the vibration plate may be damaged. Particularly, the vicinity of an edge of the opening of the vibration plate is easily damaged due to a large stress which is applied even when the vibration plate vibrates.

SUMMARY

An advantage of some aspects of the invention is to provide an ultrasonic sensor and an ultrasonic device which have an excellent flexibility, and a method of manufacturing the ultrasonic sensor.

An ultrasonic sensor according to an application example includes: a vibration plate that includes a vibration portion and is formed of a resin; a wall portion that is provided on the vibration plate, surrounds the vibration portion, and is formed of a resin; and a piezoelectric element that is provided in the vibration portion of the vibration plate.

In this application example, a wall portion formed of a resin surrounding a vibration portion of a vibration plate formed of a resin is provided, and a piezoelectric element is provided in the vibration portion of the vibration plate. The resin forming the vibration plate and the resin forming the wall portion may be different materials or may be the same material. In the application example, since the vibration plate is formed of a resin, an ultrasonic sensor excellent in flexibility can be provided. Thus, even in a case where the ultrasonic sensor is affixed to a curved object, the ultrasonic sensor can be easily bent, and breakage of the ultrasonic sensor when the ultrasonic sensor is bent can also be suppressed.

In addition, in the application example, the wall portion formed of a resin surrounding the vibration portion of the vibration plate is provided. That is, a dimension of the vibration portion of the vibration plate is defined by the wall portion, and an ultrasonic wave of a frequency corresponding to the dimension of the vibration portion can be transmitted and received. In addition, since the wall portion is formed of a resin, breakage of the wall portion when the ultrasonic sensor is bent can also be suppressed.

In the ultrasonic sensor according to the application example, it is preferable that a dimension of the wall portion in a thickness direction of the vibration plate is smaller than a dimension of the wall portion in a direction intersecting the thickness direction of the vibration plate.

In the application example with this configuration, a dimension (height) of the wall portion in a thickness direction of the vibration plate is smaller than a dimension of the wall portion intersecting a thickness of the vibration plate. The wall portion having such a configuration is strong against a stress from a direction intersecting the thickness direction of the vibration plate. That is, the wall portion formed of a resin is easily deformed in the thickness direction of the vibration plate but is hard to deform in a direction intersecting the thickness direction of the vibration plate. Thus, a dimensional variation of the vibration portion due to elastic deformation of the wall portion is suppressed, and a variation of the frequency of the ultrasonic wave to be transmitted and received can be suppressed.

In the ultrasonic sensor according to the application example, it is preferable that the ultrasonic sensor further includes a resin layer that is bonded to a surface of the wall portion on a side opposite to the vibration plate, is provided with a gap with respect to the vibration plate, and covers the vibration portion.

In the application example with this configuration, a resin layer is provided on a side opposite to the wall portion. By providing the resin layer, it is possible to attach the resin layer to an object when the ultrasonic sensor is mounted in the object.

In addition, the resin layer is configured to cover a space between the wall portions arranged with the vibration portion interposed therebetween, and thereby, it is possible to suppress a distance variation between the wall portions and to suppress a frequency variation of the ultrasonic wave to be transmitted and received.

In the ultrasonic sensor according to the application example, it is preferable that a hole that penetrates the resin layer in the thickness direction is provided at a position overlapping the vibration portion in the resin layer when viewed in the thickness direction of the vibration plate.

In the application example with this configuration, by providing holes, air in a closed space surrounded by a vibration plate, a wall portion, and a resin layer can escape to the outside. That is, in a case where no holes are provided, a vibration of the vibration plate may be obstructed by a pressure of the closed space surrounded by the vibration plate, the wall portion, and the resin layer. In contrast to this, in the application example, since the air in the closed space can escape, a vibration obstruction of the vibration portion due to an air pressure in the closed space can be suppressed.

An ultrasonic device according to an application example of the invention includes: the ultrasonic sensor described above; and a control unit that controls the ultrasonic sensor.

The ultrasonic device according to the application example includes the ultrasonic sensor described above, and the ultrasonic sensor has an excellent flexibility because both the vibration plate and the wall portion are formed of a resin. Accordingly, regardless of a surface shape of the object, it is possible to mount the ultrasonic sensor along the surface of the object and to transmit and receive an ultrasonic wave to and from the object having a complicated shape.

A method of manufacturing an ultrasonic sensor according to an application example of the invention includes: forming a piezoelectric element at a predetermined position on a first surface of a first substrate that has a Young's modulus greater than or equal to a first value and has the first surface and a second surface opposite to the first surface; forming a wall portion, which is formed of a resin and surrounds a predetermined region of the first substrate centering a position where the piezoelectric element is formed, on the first surface; forming an auxiliary layer covering the wall portion, on the first surface; bonding a second substrate having the Young's modulus greater than or equal to the first value to a surface of the auxiliary layer on a side opposite to the first substrate; removing the first substrate; forming a vibration plate that is formed of a resin at a position where the first substrate is removed, and boding the wall portion and the piezoelectric element to the vibration plate; and removing the auxiliary layer to separate the second substrate.

The method of manufacturing an ultrasonic sensor according to the application example is a method of manufacturing the ultrasonic sensor according to the application example described above. First, in a piezoelectric element forming step, a piezoelectric element is formed on a hard first substrate having a Young's modulus greater than or equal to a first value, and a wall portion forming step is performed, and thereby, a position of the wall portion with respect to the piezoelectric element is determined.

Then, in the auxiliary layer forming step, an auxiliary layer in contact with the piezoelectric element and the wall portion is formed. Thereby, the piezoelectric element and the wall portion are held by the auxiliary layer. Then, in a second substrate bonding step, a second substrate is bonded to the auxiliary layer.

Thereafter, a first substrate removing step is performed to remove the first substrate. Even in a case where the first substrate is removed, the piezoelectric element and the wall portion are held by the auxiliary layer. In addition, since the hard second substrate having the Young's modulus greater than or equal to the first value is bonded to the auxiliary layer, positions of the piezoelectric element and the wall portion are fixed (maintained).

Then, in a vibration plate forming step, a vibration plate formed of a resin is formed at a position where the first substrate is removed. Thereby, the piezoelectric element and the wall portion are bonded to the vibration plate. After that, the auxiliary layer is removed in the auxiliary layer removing step to separate the second substrate. Thereby, it is possible to easily form the ultrasonic sensor excellent in flexibility as described above.

BRIEF DESCRIPTION OF THE DRAWINGS

The invention will be described with reference to the accompanying drawings, wherein like numbers reference like elements.

DESCRIPTION OF EXEMPLARY EMBODIMENTS

First Embodiment

Hereinafter, an ultrasonic device according to a first embodiment of the invention will be described.

Figure 1:
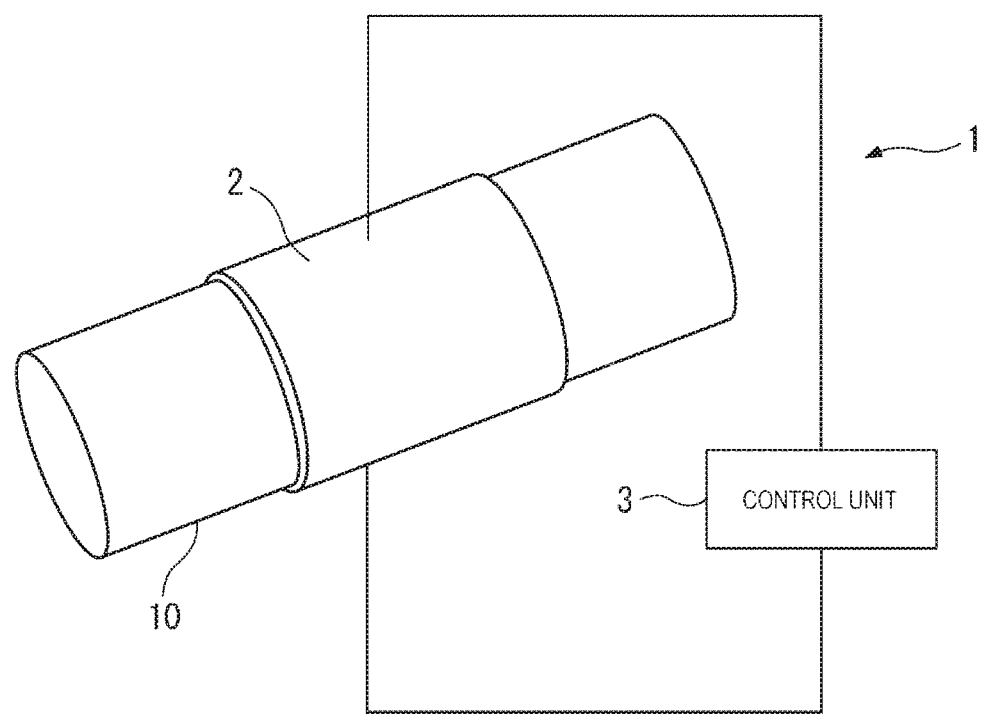
FIG. 1 is a diagram illustrating a schematic configuration of an ultrasonic device according to a first embodiment.

FIG. 1 is a diagram illustrating a schematic configuration of an ultrasonic device 1 according to the present embodiment.

As illustrated in FIG. 1, the ultrasonic device 1 according to the present embodiment includes an ultrasonic sensor 2 and a control unit 3 that controls a drive of the ultrasonic sensor 2.

The ultrasonic sensor 2 is attached to an object 10 and can be deformed depending on a shape of the object 10. For example, as illustrated in FIG. 1, in a case where the object 10 has a cylindrical shape such as a pipe, it is possible to wind the ultrasonic sensor 2 around the object 10.

By controlling the ultrasonic sensor 2 using the control unit 3, an ultrasonic wave can be transmitted from the ultrasonic sensor 2 to the object 10. By using the ultrasonic device 1, it is possible to perform various types of processing, such as internal inspection of the object 10 using transmission and reception of the ultrasonic wave, and formation of an internal tomogram.

Configuration of Ultrasonic Sensor 2

Figure 2:
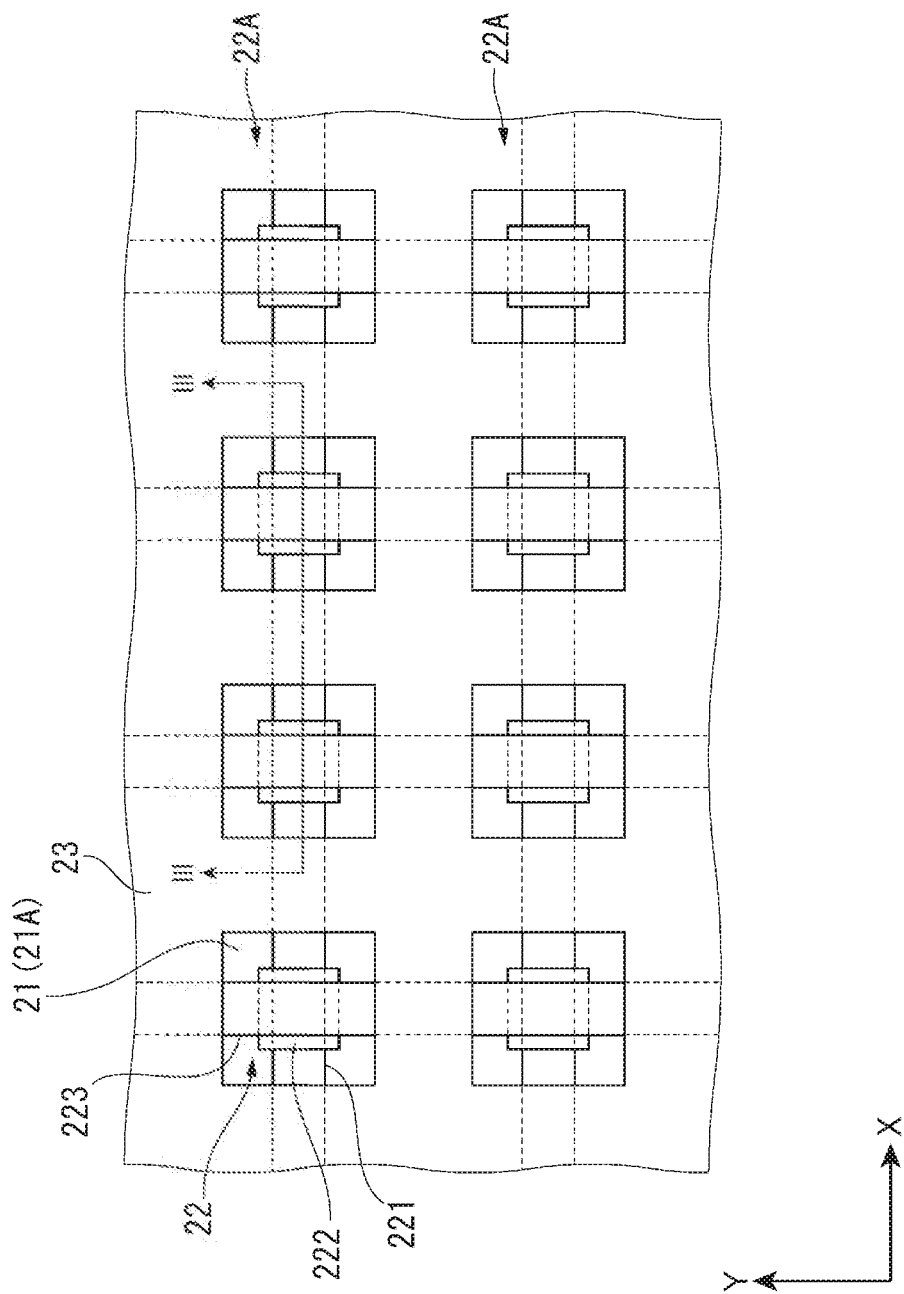
FIG. 2 is a plan view illustrating a schematic configuration of a part of the ultrasonic sensor according to the first embodiment.
Figure 3:
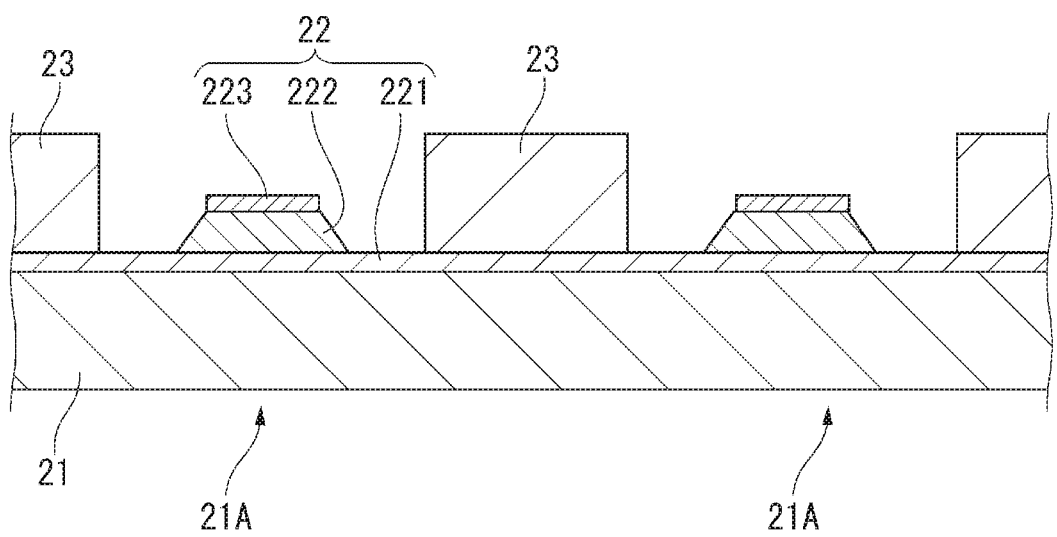
FIG. 3 is a cross-sectional view of the ultrasonic sensor of FIG. 2 cut along line A-A.
Figure 4:
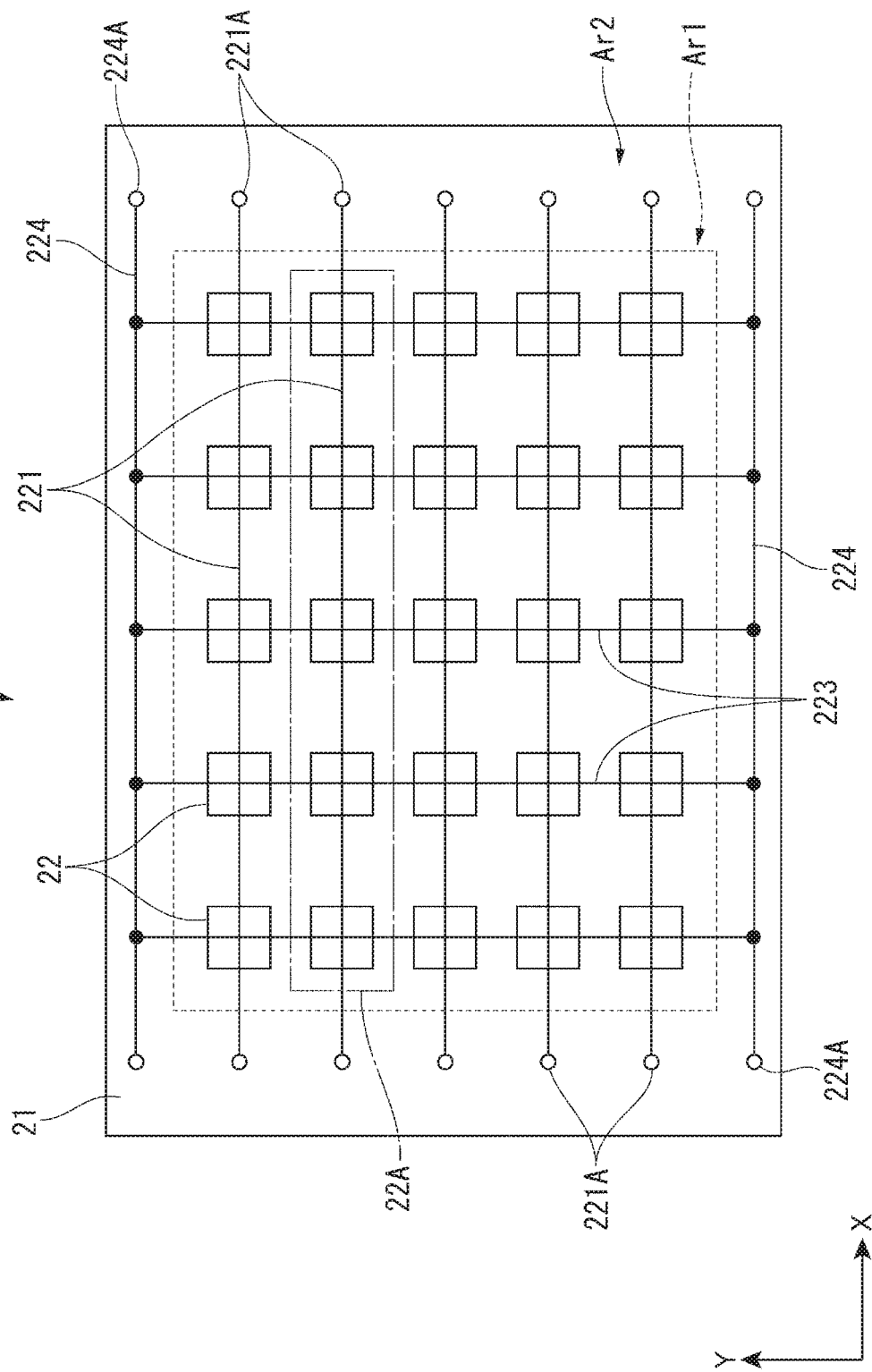
FIG. 4 is a schematic diagram illustrating a wiring configuration of the ultrasonic sensor according to the first embodiment.

FIG. 2 is a plan view illustrating a schematic configuration of a part of the ultrasonic sensor 2. FIG. 3 is a cross-sectional view of the ultrasonic sensor 2 when the ultrasonic sensor 2 in FIG. 2 is cut along line A-A. FIG. 4 is a schematic diagram illustrating a wiring configuration of the ultrasonic sensor 2. In FIG. 4, the arrangement number of the piezoelectric elements 22 is displayed in a reduced manner for the sake of convenient description, but actually, more piezoelectric elements 22 may be arranged.

As illustrated in FIG. 3, the ultrasonic sensor 2 includes a vibration plate 21 formed of a resin, a piezoelectric element 22 provided on the vibration plate 21, and a wall portion 23 provided on the vibration plate 21. In the following description, a thickness direction of the vibration plate 21 in a state where the vibration plate 21 does not vibrate is referred to as a Z direction, a direction intersecting (for example, orthogonal to) the Z direction is referred to as an X direction, and a direction intersecting (orthogonal to) the Z direction and intersecting (for example, orthogonal to) the X direction is referred to as an Y direction.

Configuration of Vibration Plate 21

The vibration plate 21 is a plate-shaped substrate having flexibility. The vibration plate 21 has a physical property of Young's modulus less than or equal to 5 GPa, and, for example, various resins such as a polyimide resin, a polypropylene resin, and a polyvinyl chloride resin can be used for the vibration plate.

As illustrated in FIG. 4, the vibration plate 21 is provided with a drive region Ar1 and an outer circumferential region Ar2. The drive region Ar1 is provided at a central portion of the vibration plate 21 when the vibration plate 21 is viewed from the Z direction, and the outer circumferential region Ar2 is provided so as to surround the drive region Ar1.

The drive region Ar1 of the vibration plate 21 is a region driven under the control of the control unit 3. A plurality of piezoelectric elements 22 are arranged in the drive region Ar1 in a two-dimensional array structure.

The outer circumferential region Ar2 is provided with terminals 221A and 224A to which drive signals for driving the drive region Ar1 are input.

Configuration of Piezoelectric Element 22

Next, the piezoelectric element 22 provided in the drive region Ar1 of the vibration plate 21 will be described.

As described above, a plurality of the piezoelectric elements 22 are provided in the drive region Ar1 of the vibration plate 21 and are arranged in a two-dimensional array shape. In the present embodiment, the piezoelectric elements 22 arranged in the X direction configure an element group 22A of one channel (1 CH) and have a structure in which a plurality of element groups 22A are arranged in the Y direction.

A specific configuration of the respective piezoelectric elements 22 will be described.

As illustrated in FIG. 3, the piezoelectric element 22 is configured by a stacked body in which a first electrode film 221, a piezoelectric film 222, and a second electrode film 223 are stacked sequentially from the vibration plate 21.

The first electrode film 221 is formed of a conductive material. For example, a metal such as Ti, Pt, Ta, Ir, Sr, In, Sn, Au, Al, Fe, Cr, Ni, or Cu, a conductive oxide typified by lanthanum nickel oxide (LNO), only one type of these materials, or a mixture or a stacked body of two types or more of these materials can be used as the conductive material. In the present embodiment, the first electrode film 221 is configured by a stacked body of Ir and Ti.

As illustrated in FIGS. 2 and 4, the first electrode film 221 is linearly formed in the X direction, and connects the respective piezoelectric elements 22 configuring the element group 22A of 1 Ch. A ±X side end portion of the first electrode film 221 configures a drive terminal 221A and is electrically connected to the control unit 3 via a lead wire, a flexible printed circuit (FPC), or the like.

The piezoelectric film 222 is configured by, for example, a piezoelectric material such as a transition metal oxide having a perovskite structure. In the present embodiment, lead zirconate titanate (PZT) containing Pb, Ti, and Zr is used as the piezoelectric film 222.

In the same manner as the first electrode film 221, the second electrode film 223 is formed of a conductive material. In the present embodiment, Ir is used as the second electrode film 223. The second electrode film 223 is linearly formed in the Y direction and connects the respective piezoelectric elements 22 aligned in the Y direction. In addition, a ±Y side end portion of the second electrode film 223 is connected to a common electrode line 224. That is, the common electrode line 224 connects a plurality of the second electrode films 223 arranged in the X direction to each other. A ±X side end portion of the common electrode line 224 configures a common terminal 224A and is electrically connected to the control unit 3 via a lead wire, an FPC, or the like.

Configuration of Wall Portion 23

The wall portion 23 is formed of a resin and is formed on the vibration plate 21 surrounding the piezoelectric elements 22 in a plan view from the Z direction. In other words, the wall portion 23 is formed by stacking a resin having openings of a predetermined dimension centering the piezoelectric elements 22 on the vibration plate 21. A resin material forming the wall portion 23 may be the same as the resin material forming the vibration plate 21 or may be a different resin.

In addition, a dimension (height) of the wall portion 23 in the Z direction is sufficiently smaller than each dimension of the wall portion 23 in an XY plane direction. For example, in the present embodiment, a thickness of the piezoelectric element 22 is 3 μm, a dimension of the wall portion 23 in the Z direction is 5 μm, and a dimension (width) of the wall portion 23 in the X direction and the Y direction is 30 μm. Such a wall portion 23 is hard to elastically deform in the X direction and the Y direction with respect to the Z direction and is easy to elastically deform in the Z direction. That is, as the wall portion 23 deforms elastically and largely in the Z direction, the ultrasonic sensor 2 can be made to follow a curved surface of the object 10. In addition, since the wall portion 23 is hard to elastically deform in the X direction and the Y direction, a size of a portion (vibration portion 21A), which is surrounded by the wall portion 23 of the vibration plate 21, in the X direction and the Y direction is hard to vary.

However, if a voltage is applied between the first electrode film 221 and the second electrode film 223 of the piezoelectric element 22 to drive the piezoelectric film 222, the vibration portion 21A surrounded by the wall portion 23 of the vibration plate 21 centering the piezoelectric element 22 vibrates to transmit an ultrasonic wave. At this time, the ultrasonic wave is transmitted by vibrating the vibration portion 21A at a natural frequency corresponding to a shape (dimension) of the vibration portion 21A.

In addition, if the ultrasonic wave is input to the ultrasonic sensor 2, the vibration portion 21A vibrates, and thereby, a potential difference occurs on the first electrode film 221 side and the second electrode film 223 side of the piezoelectric film 222, and a signal (received signal) is output. By detecting the reception signal, reception of the ultrasonic wave can be detected by the ultrasonic sensor 2. At this time, when the ultrasonic wave having the same (or substantially the same) frequency as the natural frequency of the vibration portion 21A is received, a displacement of the vibration portion 21A increases and the vibration portion 21A can detect the reception of the ultrasonic wave with a high accuracy.

As such, the frequency of the ultrasonic wave output from the ultrasonic sensor 2 is strongly influenced by a size of the vibration portion 21A. Here, in a case where the vibration portion 21A is circular, the frequency of the ultrasonic waves is mainly determined by a diameter of the vibration portion 21A, and in a case where a shape of the vibration portion 21A is a shape having a long axis and a short axis (a rectangle, an ellipse or the like), the frequency of the ultrasonic waves is mainly determined by a dimension in the short axis direction. That is, the ultrasonic wave to be transmitted and received by the ultrasonic sensor 2 is determined by a minimum distance between the wall portions 23 interposing the vibration portion 21A, in a plan view of the vibration plate 21 as viewed from the Z direction.

Thus, in the present embodiment, the wall portion is formed such that the natural frequency of the vibration portion 21A is the frequency of the ultrasonic wave to be transmitted and received by the ultrasonic sensor 2. In addition, as described above, the wall portion 23 is hard to elastically deform in the X direction and the Y direction. Accordingly, even in a case where the ultrasonic sensor 2 is bent along the object 10, for example, a frequency variation of the ultrasonic wave to be transmitted and received by the ultrasonic sensor 2 is suppressed.

Configuration of Control Unit 3

The control unit 3 is connected to terminals 221A and 224A of the ultrasonic sensor 2, and is configured by a circuit that controls drive of the ultrasonic sensor 2. The control unit 3 may be a personal computer or the like in which a drive driver circuit of the ultrasonic sensor 2 is incorporated or may be a dedicated control device that controls the drive of the ultrasonic sensor 2.

Specifically, the control unit 3 outputs a drive signal for applying a cyclic drive voltage to the terminals 221A and 224A of the ultrasonic sensor 2 and causes the ultrasonic sensor 2 to output the ultrasonic wave to the object 10. In addition, the control unit 3 acquires a reception signal when each piezoelectric element 22 is displaced by the ultrasonic wave received by the ultrasonic sensor 2. Furthermore, the control unit 3 may measure a distance from the ultrasonic sensor 2 to a reflection position of the ultrasonic wave, based on the received signal.

Flexibility of Ultrasonic Sensor 2

Figure 5:
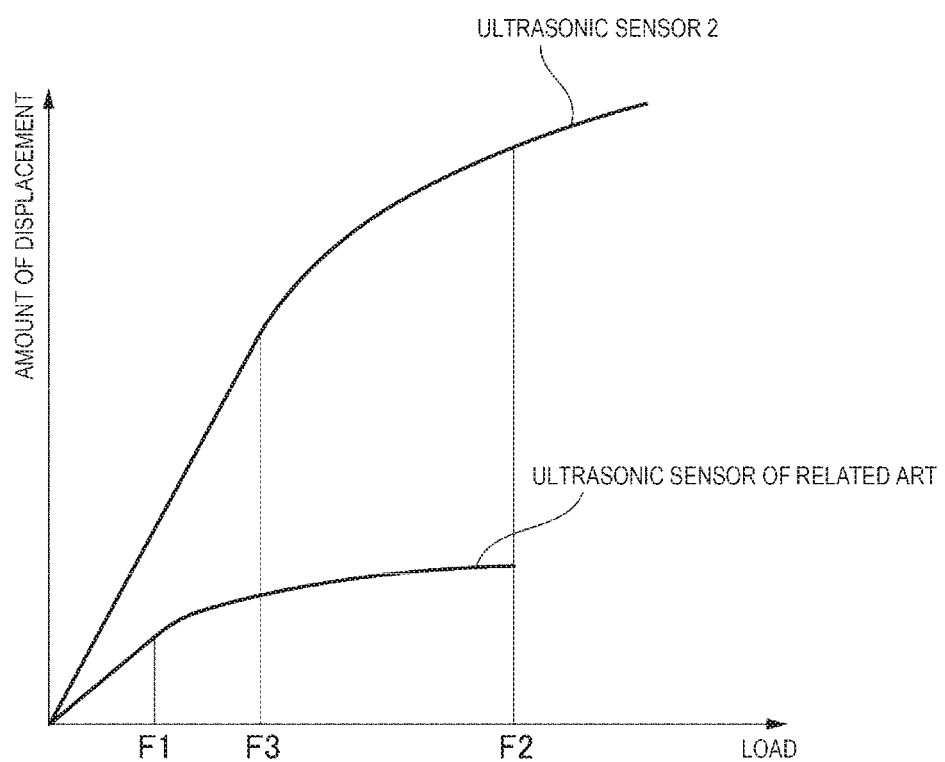
FIG. 5 is a diagram illustrating a comparison between a strength of the ultrasonic sensor according to the first embodiment and a strength of the ultrasonic sensor of the related art.

FIG. 5 is a diagram illustrating a comparison between a strength of an ultrasonic sensor of the related art and the ultrasonic sensor 2 according to the present embodiment. A sensor in which an opening is formed in a Si substrate, a vibration plate configured by a stacked body of $SiO_2$ and $ZrO_2$ is provided so as to cover the opening, and a piezoelectric element is provided in each opening of the vibration plate is used as the ultrasonic sensor of the related art.

In the ultrasonic sensor of the related art, if a voltage is applied to the piezoelectric element and a load is applied to the vibration plate, the amount of displacement increases substantially and linearly with respect to the load up to a predetermined first limit point F1. However, if the load exceeds the first limit point F1, a change in the displacement amount with respect to the load becomes nonlinear and an increase rate of the displacement amount is reduced. Furthermore, if the load reaches a second limit point F2, a breakage such as a crack occurs in the vibration plate.

Meanwhile, in the ultrasonic sensor 2 according to the present embodiment, when a load is applied to the vibration plate 21 by applying a voltage to the piezoelectric element 22, a range in which the amount of displacement of the vibration plate 21 is linearly changed with respect to the load becomes wider. That is, the first limit point F3 of the ultrasonic sensor 2 according to the present embodiment is larger than the first limit point F1 of the related art. This means that when a predetermined voltage is applied to the piezoelectric element 22, the ultrasonic sensor 2 according to the present embodiment can output an ultrasonic wave of a larger sound pressure.

In addition, also in the ultrasonic sensor 2 according to the present embodiment, after the load exceeds the first limit point F3, an increase rate of the amount of displacement gradually decreases and the amount of displacement changes nonlinearly. However, as illustrated in FIG. 5, the change is gentle, and there is no sharp decrease in the amount of displacement as in the ultrasonic sensor of the related art. Furthermore, in the ultrasonic sensor 2 according to the present embodiment, a breakage does not occur even if the ultrasonic sensor of the related art exceeds the second limit point F2 at which the breakage occurs. That is, the second limit point at which the breakage occurs in the ultrasonic sensor 2 according to the present embodiment is much larger than the second limit point of the ultrasonic sensor of the related art. That is, the vibration plate 21 and the wall portion 23 formed of a resin have a higher elastic deformability than the substrate of the related art formed of Si, or the vibration plate of the related art configured by a stacked body of $SiO_2$ and $ZrO_2$, and the breakages of the vibration plate 21 and the wall portion 23 due to a crack or the like are suppressed.

In addition, in the ultrasonic sensor of the related art, if the ultrasonic sensor is mounted along a curved surface of the object 10 having a curved surface having a curvature larger than or equal to a predetermined curvature, a crack (cracking) may occur in the Si substrate or the vibration plate.

In contrast to this, in the ultrasonic sensor 2 according to the present embodiment, the vibration plate 21 is formed of a resin and the wall portion 23 formed of a resin is used instead of the Si substrate having the opening of the related art. Thus, the ultrasonic sensor 2 is excellent in elastic deformability compared with the ultrasonic sensor of the related art, and the ultrasonic sensor 2 is moved along the curved surface without breakage regardless of a curvature of the curved surface of the object 10.

Method of Manufacturing Ultrasonic Sensor 2

Next, a method of manufacturing the ultrasonic sensor 2 described above will be described.

Figure 6:
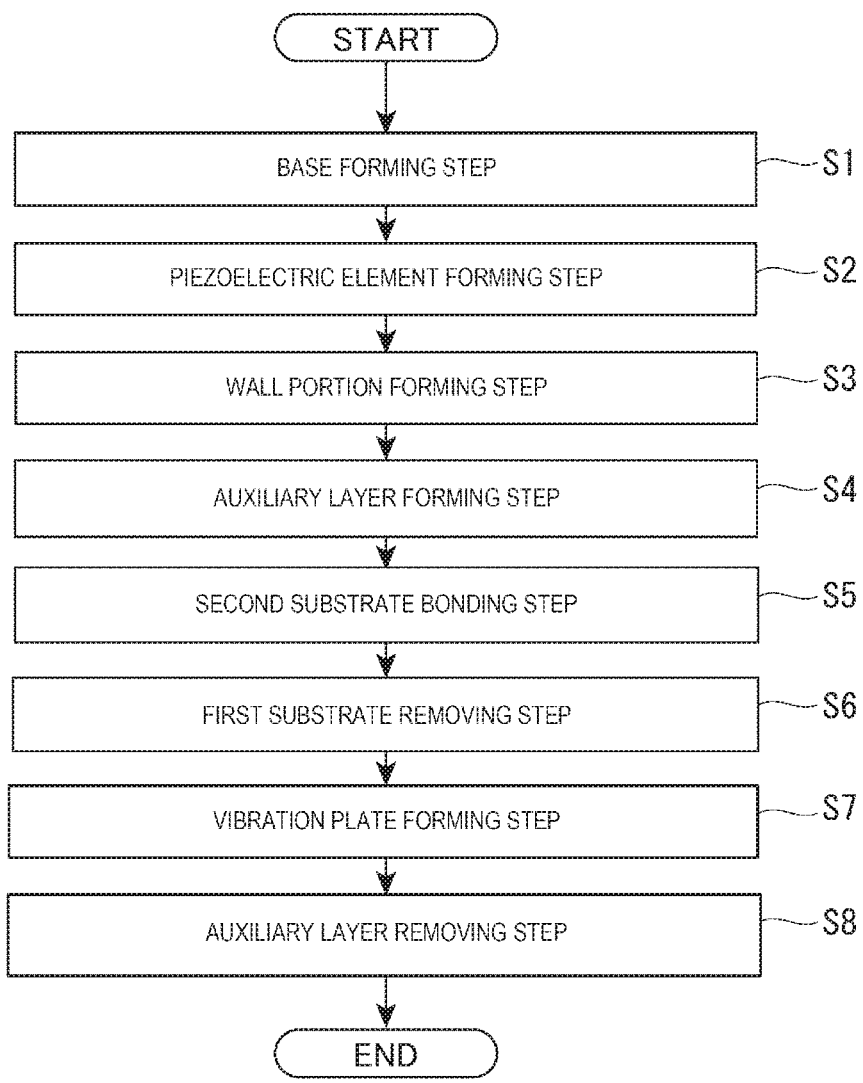
FIG. 6 is a flowchart illustrating a method of manufacturing the ultrasonic sensor according to the first embodiment.

FIG. 6 is a flowchart illustrating the method of manufacturing the ultrasonic sensor 2.

Figure 7:
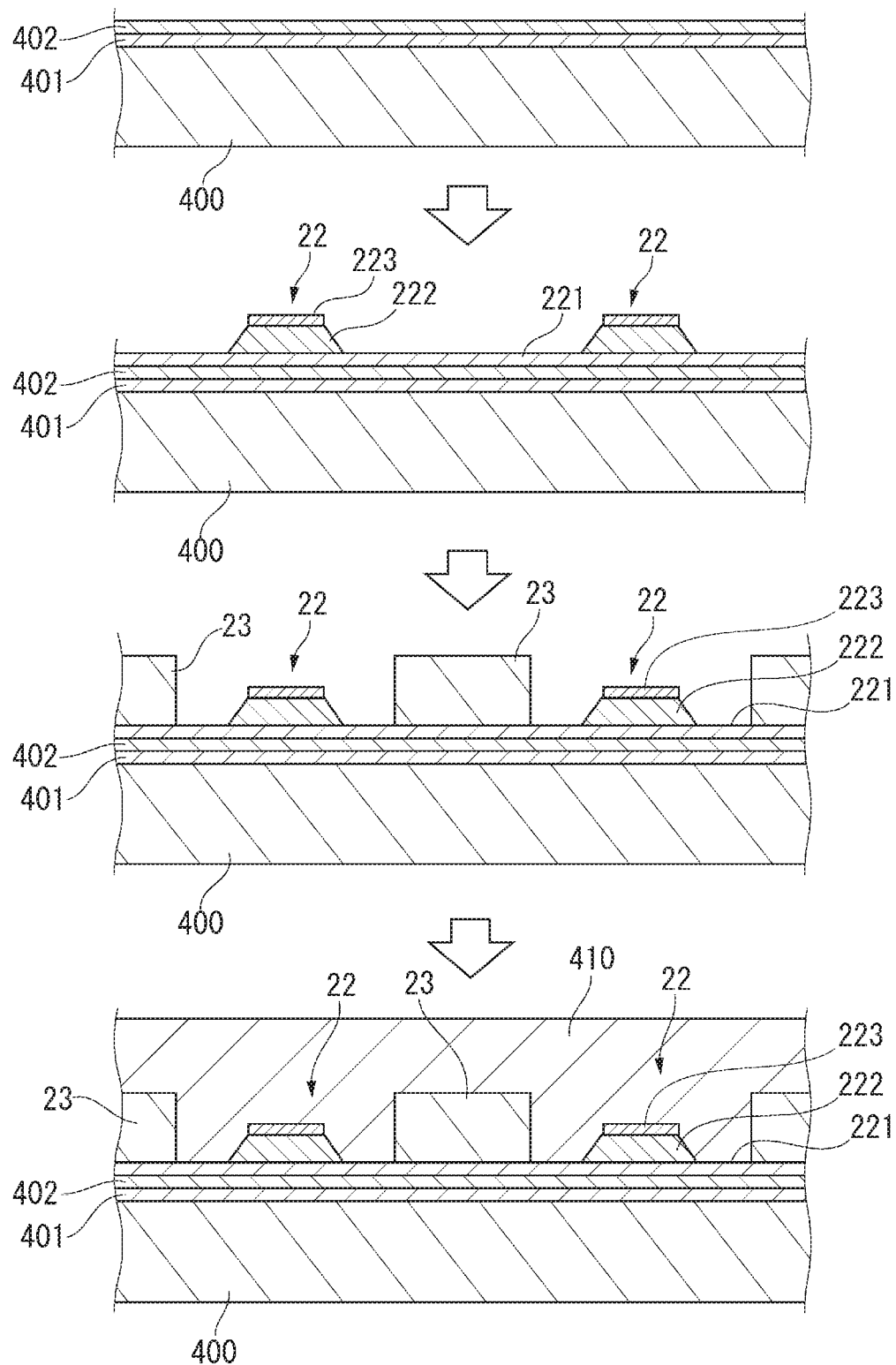
FIG. 7 is a diagram illustrating steps from a base forming step to an auxiliary layer forming step in a method of manufacturing the ultrasonic sensor.
Figure 8:
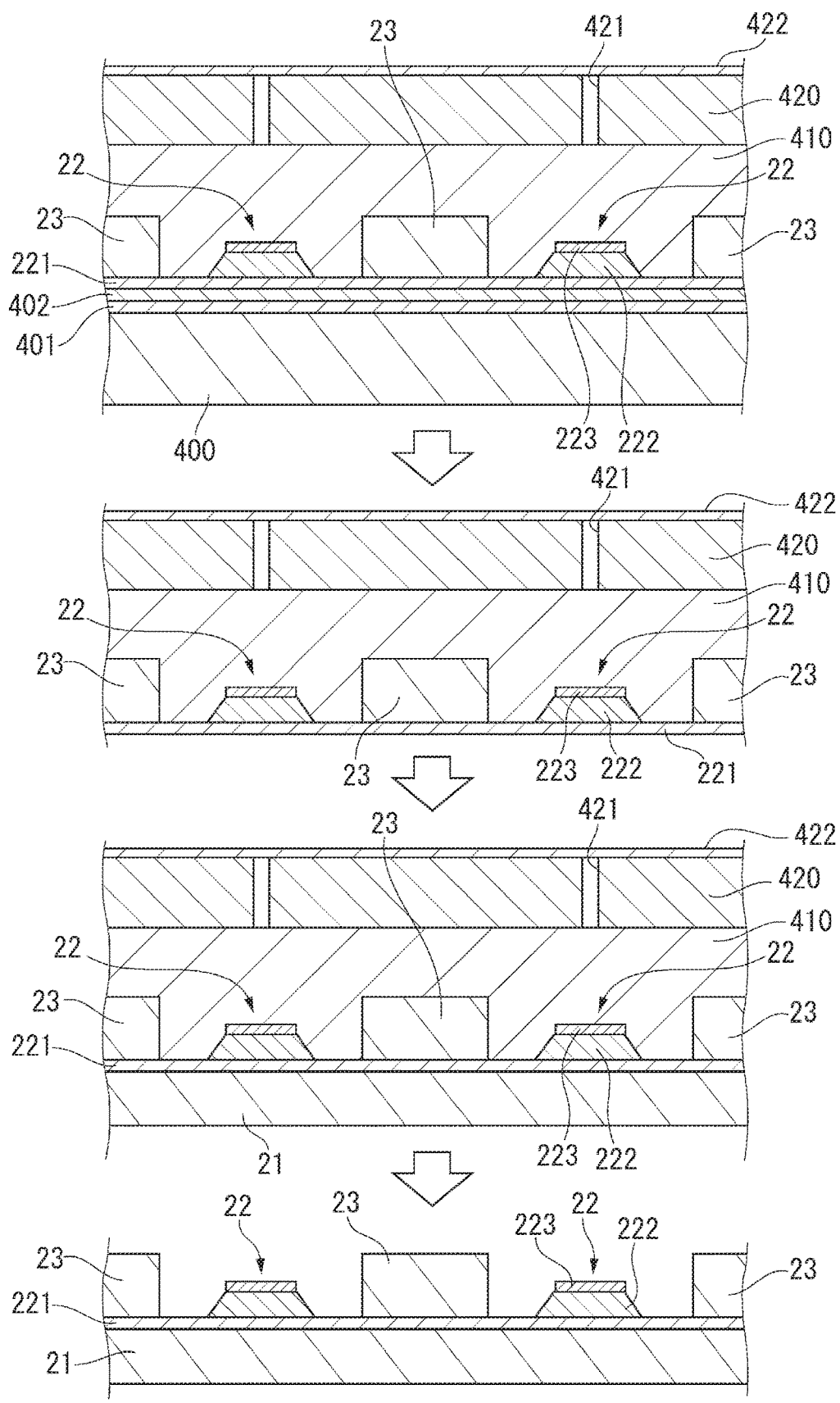
FIG. 8 is a diagram illustrating steps from a second substrate bonding step to an auxiliary layer removing step in the method of manufacturing the ultrasonic sensor.

As illustrated in FIG. 6, in a case where the ultrasonic sensor 2 is manufactured, a base forming step S1, a piezoelectric element forming step S2, a wall portion forming step S3, an auxiliary layer forming step S4, a second substrate bonding step S5, a first substrate removing step S6, a vibration plate forming step S7, and an auxiliary layer removing step S8 are implemented. FIG. 7 is a diagram illustrating steps from the base forming step S1 to the auxiliary layer forming step S4, and FIG. 8 is a diagram illustrating steps from the second substrate bonding step S5 to the auxiliary layer removing step S8.

In the base forming step S1, a first substrate 400 formed (hard to elastically deform) of a hard material in which Young's modulus is greater than or equal to a predetermined first value (for example, 100 GPa) is prepared. In the present embodiment, the first substrate 400 is configured by a Si substrate.

Then, one surface side of the first substrate 400 of Si is thermally oxidized to form a $SiO_2$ film 401 on a surface of the first substrate 400. Furthermore, a Zr layer is formed on the $SiO_2$ film 401, which is thermally oxidized to form a $ZrO_2$ layer 402 as illustrated in the first part of FIG. 7. A surface of the $ZrO_2$ layer 402 configures the first surface of the first substrate 400 and a surface of the first substrate 400 opposite to the surface on which the $ZrO_2$ layer 402 is formed configures the second surface.

In the piezoelectric element forming step S2, the piezoelectric element 22 is formed in a predetermined position on the $ZrO_2$ layer 402 of the first substrate 400, as illustrated in the second part of FIG. 7.

In the piezoelectric element forming step S2, a stacked electrode of Ir and Ti is formed on the $ZrO_2$ layer 402 by sputtering or the like, and the first electrode film 221 is formed by etching or the like.

Furthermore, a piezoelectric film 222 is formed on the first electrode film 221. The piezoelectric film 222 can be formed by, for example, a solution method. A piezoelectric film having a predetermined thickness is formed by performing a plurality of times, for example, a coating step of applying a PZT solution so as to cover the $ZrO_2$ layer 402 and the first electrode film 221, and a baking step of baking the applied PZT solution, and the piezoelectric film 222 is formed by performing patterning due to etching. In a case where the piezoelectric element is formed on the $ZrO_2$ layer 402 as in the present embodiment, diffusion of Pb atoms contained in the piezoelectric film 222 (PZT) is suppressed, and performance deterioration of the piezoelectric element 22 is suppressed.

Thereafter, an Ir layer covering the first electrode film 221, the piezoelectric film 222, and the $ZrO_2$ layer 402 is formed by sputtering or the like, and is patterned by etching or the like to form the second electrode film 223.

In the wall portion forming step S3, the wall portion 23 surrounding a predetermined region centering a position where the piezoelectric element 22 is formed is formed on the $ZrO_2$ layer 402 side of the first substrate 400, as illustrated in the third part in FIG. 7. The wall portion 23 is formed, for example, by forming a resin on the $ZrO_2$ layer 402 side of the first substrate 400 and patterning the resin by etching or the like.

In the auxiliary layer forming step S4, the auxiliary layer 410 formed of a resist or the like is formed on the entire $ZrO_2$ layer 402 side of the first substrate 400, as illustrated in the fourth part in FIG. 7. Thereby, the piezoelectric element 22 and the wall portion 23 formed on the $ZrO_2$ layer 402 side of the first substrate 400 are in contact with the auxiliary layer 410 and held by the auxiliary layer 410. Since the auxiliary layer 410 is dissolved and removed later, it is preferable to use a readily dissolvable material such as a positive photoresist.

In the second substrate bonding step S5, the second substrate 420 formed of, for example, Si is bonded to a surface of the auxiliary layer 410 on the side opposite to the first substrate 400, as illustrated in the first part of FIG. 8.

In the same manner as the first substrate 400, the second substrate 420 is a substrate having a Young's modulus greater than or equal to a first value (for example, 100 GPa). The second substrate 420 is provided with a through-hole 421 penetrating from a surface of the auxiliary layer 410 side to a surface opposite to the auxiliary layer 410. It is preferable that the through-hole 421 is provided at a position facing the piezoelectric element 22, as illustrated in the first part in FIG. 8.

Furthermore, in the second substrate bonding step S5, a protective film 422 is formed on a side of the bonded second substrate 420 opposite to the auxiliary layer 410. The protective film 422 is formed to prevent the second substrate 420 from being etched when the first substrate 400 formed of Si is removed by etching. Thus, a film resistant to an etching solution of the Si substrate is used as the protective film 422.

Here, although the protective film 422 is formed after the second substrate 420 is bonded to the auxiliary layer 410, the invention is not limited to this. For example, the second substrate 420 having the protective film 422 formed on a surface other than a surface bonded to the auxiliary layer 410 may be bonded to the auxiliary layer 410.

In the first substrate removing step S6, the first substrate 400 is removed, as illustrated in the second part of FIG. 8. Removal of the first substrate 400 may be removal of the first substrate 400 by using etching, or removal made by cutting processing, polishing processing, or the like.

Since the piezoelectric element 22 and the wall portion 23 are held by the auxiliary layer 410 and the second substrate 420 even after the first substrate 400 is removed, a relative positional relationship between the piezoelectric element 22 and the wall portion 23 is maintained.

Thereafter, a resin is applied to surfaces of the piezoelectric element 22, the wall portion 23, and the auxiliary layer 410 on a side opposite to the second substrate 420 to form the vibration plate 21, as illustrated in a third part of FIG. 8. Thereby, the piezoelectric element 22 and the wall portion 23 are bonded to the vibration plate 21.

Then, the protective film 422 is removed, and a dissolution liquid for removing the resist (auxiliary layer 410) is injected from the through-hole 421 of the second substrate 420. Thereby, as illustrated in a fourth part of FIG. 8, the auxiliary layer 410 is dissolved and removed, and the second substrate 420 is peeled off, and thereby, manufacturing the ultrasonic sensor 2 is completed.

Action Effect of Present Embodiment

In the ultrasonic sensor 2 according to the present embodiment, the wall portion 23 formed of a resin is provided so as to surround the vibration portion 21A of the vibration plate 21 formed of the resin, and the piezoelectric elements 22 are provided inside the vibration portion 21A of the vibration plate 21. In this way, by forming the vibration plate 21 and the wall portion 23 with the resin, it is possible to provide the ultrasonic sensor 2 excellent in flexibility, to suitably mount the ultrasonic sensor 2 even onto a curved object, and to suppress a damage to the ultrasonic sensor 2 as well.

In the ultrasonic sensor 2 according to the present embodiment, the dimension (height) of the wall portion 23 in the Z direction is smaller than the dimensions (widths) of the wall portion 23 in the X direction and the Y direction. Since the wall portion 23 having such a configuration can be deformed easily and elastically by a stress in the Z direction, the ultrasonic sensor 2 can be easily deformed depending on a shape of the object 10. Meanwhile, the wall portion 23 is hard to deform elastically with respect to the stress in the X direction and the Y direction, and a dimensional variation of the vibration portion 21A can be suppressed.

That is, even in a case where both the vibration plate 21 and the wall portion 23 are formed of a resin as in the present embodiment, the dimensional variation of the vibration portion 21A due to an elastic deformation of the wall portion 23 is suppressed, and a variation of the frequency of the ultrasonic wave to be transmitted and received can be suppressed.

In the present embodiment, after the piezoelectric element 22 and the wall portion 23 are formed on the first substrate 400 in the piezoelectric element forming step S2 and the wall portion forming step S3, the auxiliary layer 410 covering the piezoelectric elements 22 and the wall portion 23 is formed in the auxiliary layer forming step S4. Thereby, the piezoelectric element 22 and the wall portion 23 are held by the auxiliary layer 410. Accordingly, when the first substrate 400 is removed in the first substrate removing step S6, the piezoelectric element 22 and the wall portion 23 are not separated, or a positional relationship between the piezoelectric element 22 and the wall portion 23 is not collapsed. Furthermore, the auxiliary layer 410 is bonded to the second substrate 420 in the second substrate bonding step. Accordingly, even after the first substrate 400 is removed in the first substrate removing step S6, the shape of the auxiliary layer is maintained by the second substrate 420, and the relative positional relationship between the piezoelectric element 22 and the wall portion 23 is also maintained. Accordingly, it is possible to easily manufacture the ultrasonic sensor 2 capable of transmitting and receiving a predetermined frequency with a high accuracy.

Second Embodiment

Next, an ultrasonic sensor according to the second embodiment will be described.

The second embodiment is different from the first embodiment in that a resin layer is further provided on a side of the wall portion 23 opposite to the vibration plate in the ultrasonic sensor 2 according to the first embodiment. In the following description, the same reference numerals or symbols are attached to the items previously described, and description thereof will be omitted or simplified.

Figure 9:
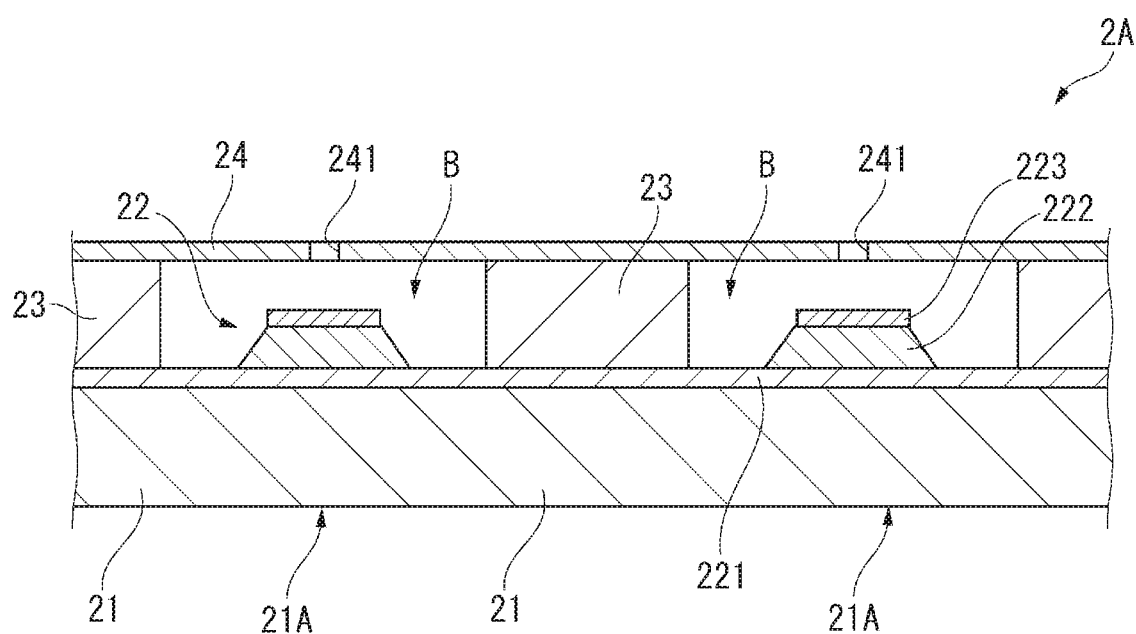
FIG. 9 is a sectional view illustrating a schematic configuration of an ultrasonic sensor according to a second embodiment.

FIG. 9 is a schematic sectional view of the drive region Ar1 of an ultrasonic sensor 2A according to the present embodiment.

In the same manner as in the first embodiment, the ultrasonic sensor 2A according to the present embodiment includes the vibration plate 21 formed of a resin, the piezoelectric element 22, and the wall portion 23 formed of a resin. The ultrasonic sensor 2A further includes a resin layer 24 formed to cover a surface of the wall portion 23 opposite to the vibration plate 21.

The resin layer 24 is, for example, a resin formed in a sheet shape and is formed by being bonded to the wall portion 23 in a lamination process. That is, the resin layer 24 is provided on a side of the wall portion 23 opposite to the vibration plate 21 and is disposed to be opposite to the vibration portion 21A via a gap (space B).

Providing the resin layer 24 is advantageous, for example, when the ultrasonic sensor 2A is fixed to an object to be mounted. For example, in a case where the ultrasonic sensor 2A illustrated in FIG. 9 is mounted on the object 10 as illustrated in FIG. 1, the resin layer 24 is brought into close contact with the object 10. In this case, a surface area in contact with the object 10 increases as compared with a case where only the wall portion 23 is brought into close contact with the object 10. Thus, inconvenience and the like that the ultrasonic sensor 2A is separated from the object 10 are suppressed.

In addition, as illustrated in FIG. 9, a configuration may be adopted in which holes 241 are provided at positions facing the vibration portion 21A in the resin layer 24.

If the resin layer 24 is formed so as to cover the wall portion 23, a space B surrounded by the vibration plate 21, the wall portion 23, and the resin layer 24 is a sealed space. In this case, vibration of the vibration portion 21A is obstructed by an air pressure in the space B. In contrast to this, by providing the holes 241, air in the space B can escape to the outside, and the vibration obstruction of the vibration portion 21A due to the air pressure is suppressed.

Action Effect of Present Embodiment

In the ultrasonic sensor 2A according to the present embodiment, the resin layer 24 is formed in the surface of the wall portion 23 opposite to the vibration plate 21. By providing the resin layer 24, the resin layer can be attached to the object 10 when the ultrasonic sensor 2A is mounted on the object 10. In this case, a surface area of the ultrasonic sensor 2A in contact with the object 10 increases, and inconvenience and the like that the ultrasonic sensor 2A is separated from the object 10 can be suppressed.

In addition, since the resin layer 24 is configured to cover spaces between the wall portions 23 arranged to surround the vibration portion 21A, it is possible to further suppress a distance variation between the wall portions 23 and to suppress a frequency variation of the ultrasonic wave to be transmitted and received.

In the ultrasonic sensor 2A according to the present embodiment, the holes 241 are provided at positions facing the vibration portion 21A of the resin layer 24. Accordingly, the air in the space B surrounded by the vibration plate 21, the wall portion 23, and the resin layer 24 can escape to the outside, and the inconvenience that the vibration of the vibration plate 21 due to the pressure of the space B is obstructed can be suppressed.

Modification Example

The invention is not limited to the respective embodiments described above, and a configuration obtained by modifications, improvements, appropriate combination of the respective embodiments, and the like within a range in which the object of the invention can be attained are included in the invention.

In the ultrasonic sensor 2 according to the first embodiment described above, a configuration is used in which the wall portion 23 is provided on a side of the vibration plate 21 on which the piezoelectric element 22 is provided, but the configuration is not limited to this. That is, the wall portion 23 may be provided at a position surrounding the vibration portion 21A of the vibration plate 21.

The examples illustrated in FIGS. 10 to 13 are diagrams illustrating another example of the ultrasonic sensor according to the invention.

Figure 10:
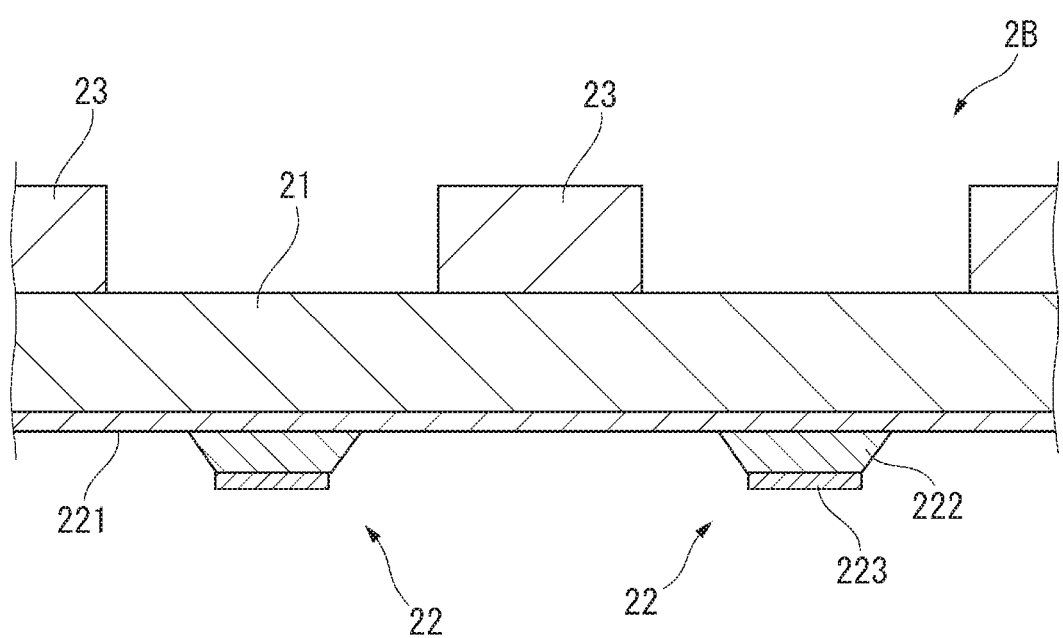
FIG. 10 is a sectional view illustrating a schematic configuration of an ultrasonic sensor according to a modification example.

For example, as in an ultrasonic sensor 2B illustrated in FIG. 10, a configuration may be provided in which the piezoelectric element 22 is provided on the surface (surface on a +Z side) on one side of the vibration plate 21, and the wall portion 23 is provided on a surface (surface on a −Z side) on the other side of the vibration plate 21.

Figure 11:
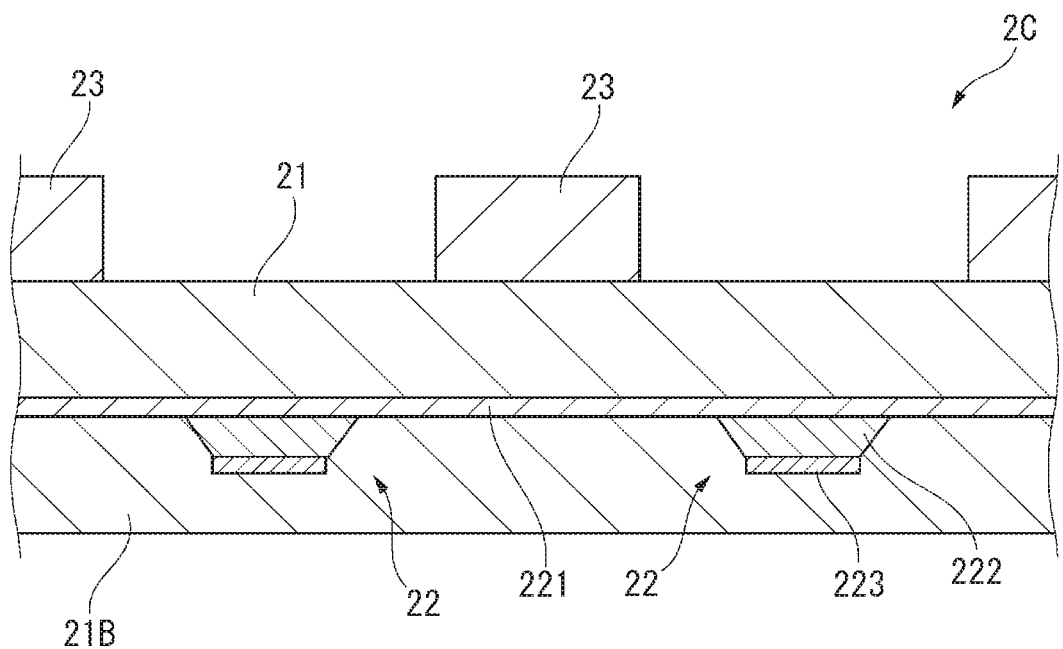
FIG. 11 is a sectional view illustrating a schematic configuration of an ultrasonic sensor according to another modification example.

In addition, an ultrasonic sensor 2C illustrated in FIG. 11 is an example in which a protective layer 21B which is formed of a resin and covers the piezoelectric element 22 is further provided on the surface on the +Z side of the ultrasonic sensor 2B illustrated in FIG. 10. In this case, the piezoelectric element 22 is covered with the resin, and thereby, water resistance can be improved.

Figure 12:
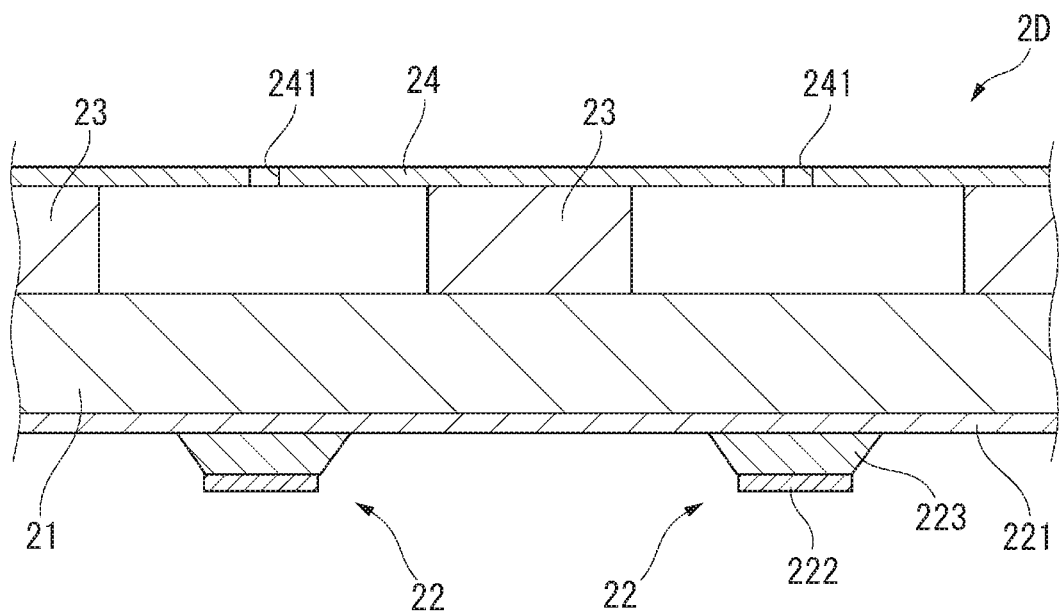
FIG. 12 is a sectional view illustrating a schematic configuration of an ultrasonic sensor according to still another modification example.

Furthermore, an ultrasonic sensor 2D illustrated in FIG. 12 is an example in which the resin layer 24 which is the same as the resin layer in the second embodiment is formed on a surface of the wall portion 23 of the ultrasonic sensor 2B illustrated in FIG. 10 on the side opposite to the vibration plate 21. In this case, in the same manner as in the second embodiment, when the ultrasonic sensor 2D is mounted on the object 10, a surface area of the mounting surface can increase.

Figure 13:
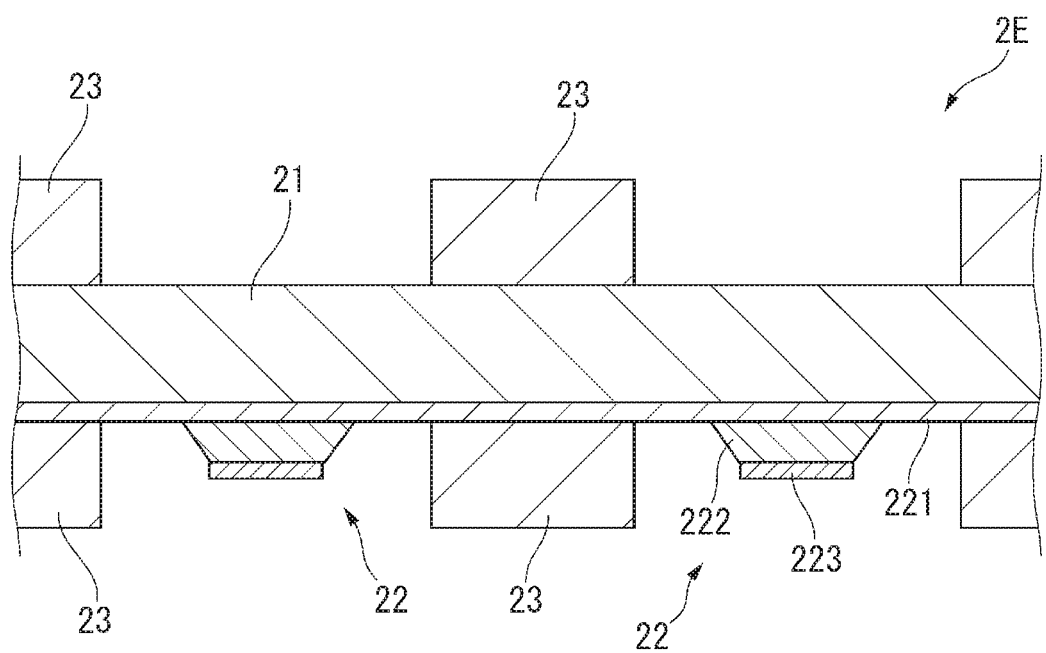
FIG. 13 is a sectional view illustrating a schematic configuration of an ultrasonic sensor according to still another modification example.

Furthermore, as in an ultrasonic sensor 2E illustrated in FIG. 13, the wall portion 23 may be provided on both the +Z side and the −Z side of the vibration plate 21. In this case, it is possible to further suppress a dimensional variation of the vibration portion 21A, and to more reliably suppress a frequency variation of an ultrasonic wave to be transmitted and received.

In addition, the respective ultrasonic sensors 2, 2A, 2B, 2C, 2D, and 2E described above may transmit and receive ultrasonic waves to and from a side where the wall portion 23 is provided by using the vibration of the vibration portion 21A of the vibration plate 21, and may transmit and receive the ultrasonic wave on a side opposite to the side on which the wall portion 23 is provided.

The example illustrated in FIG. 1 is an example in which the ultrasonic wave is transmitted and received to and from the object 10, but, for example, a configuration may be used in which the ultrasonic sensors 2, 2A, 2B, 2C, 2D, and 2E are fixed to a support body and the ultrasonic wave is transmitted and received to and from a side opposite to the support body.

In the first embodiment, the example in which the piezoelectric element 22 arranged in a two-dimensional array structure is provided in the drive region Ar1 of the ultrasonic sensor 2 is illustrated, but the invention is not limited to this. For example, the piezoelectric elements may be arranged in a one-dimensional array structure at a predetermined distance interval.

Besides, a specific structure at the time of practicing the invention may be configured by appropriately combining each of the embodiments and modification examples within a range in which the object of the invention can be attained and may be appropriately changed to other structures and the like.

The entire disclosure of Japanese Patent Application No. 2018-028546, filed Feb. 21, 2018 is expressly incorporated by reference herein.

What is claimed is:

1. An ultrasonic sensor comprising:
    a vibration plate that includes a vibration portion and is formed of a resin;
    a wall portion that is provided on the vibration plate, surrounds the vibration portion, and is formed of a resin; and
    a piezoelectric element that is provided in the vibration portion of the vibration plate.

2. The ultrasonic sensor according to claim 1,
    wherein a dimension of the wall portion in a thickness direction of the vibration plate is smaller than a dimension of the wall portion along a direction intersecting the thickness direction of the vibration plate.

3. The ultrasonic sensor according to claim 1, further comprising:
    a resin layer that is bonded to a surface of the wall portion on a side opposite to the vibration plate, is provided with a gap with respect to the vibration plate, and covers the vibration portion.

4. The ultrasonic sensor according to claim 3,
    wherein a hole that penetrates the resin layer in the thickness direction is provided at a position overlapping the vibration portion in the resin layer when viewed in the thickness direction of the vibration plate.

5. An ultrasonic device comprising:
    the ultrasonic sensor according to claim 1; and
    a control unit that controls the ultrasonic sensor.

6. An ultrasonic device comprising:
    the ultrasonic sensor according to claim 2; and
    a control unit that controls the ultrasonic sensor.

7. An ultrasonic device comprising:
    the ultrasonic sensor according to claim 3; and
    a control unit that controls the ultrasonic sensor.

8. An ultrasonic device comprising:
    the ultrasonic sensor according to claim 4; and
    a control unit that controls the ultrasonic sensor.

* * * * *